United States Patent [19]

Couetil

[11] Patent Number: 4,829,985

[45] Date of Patent: May 16, 1989

[54] STERNAL RETRACTOR

[75] Inventor: Jean-Paul A. Couetil, Paris, France

[73] Assignee: Delacroix-Chevalier, France

[21] Appl. No.: 54,734

[22] Filed: May 27, 1987

[30] Foreign Application Priority Data

May 28, 1986 [FR] France .................................. 86 07624

[51] Int. Cl.⁴ ............................................. A61B 17/02
[52] U.S. Cl. ................................................... 128/20
[58] Field of Search ........................... 128/3, 17, 18, 20

[56] References Cited

U.S. PATENT DOCUMENTS

| 2,450,194 | 9/1948 | Glaser | 128/20 |
| 2,642,862 | 6/1953 | Jackson | 128/20 |
| 2,693,795 | 11/1954 | Grieshaber | 128/20 |
| 3,747,592 | 7/1973 | Santos | 128/20 |
| 3,810,462 | 5/1974 | Szpur | 128/20 |
| 4,344,420 | 8/1982 | Forder | 128/20 |
| 4,617,916 | 10/1986 | LeVahn | 128/20 |
| 4,627,421 | 12/1986 | Symbas et al. | 128/20 |
| 4,702,230 | 10/1987 | Pelta | 128/20 |

FOREIGN PATENT DOCUMENTS

| 1019217 | 1/1953 | France | 128/20 |
| 2302078 | 9/1976 | France | 128/20 |

Primary Examiner—Edward M. Coven
Assistant Examiner—Mark S. Graham

[57] ABSTRACT

A sternal retractor formed of a toothed rack having two arms supporting blades, wherein one of the arms carries a removable bearing blade whose axis is in a plane forming an angle of 30° to 60° with the plane of the rack and the other arm is a round rod carrying two removable blades in the form of closed, loosely fitted claws. The retractor is designed to be reversible.

10 Claims, 1 Drawing Sheet

U.S. Patent      May 16, 1989      4,829,985
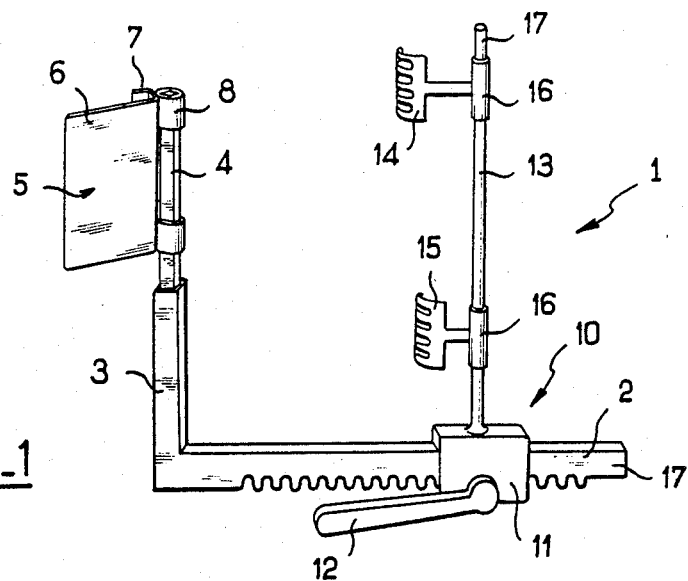
FIG_1
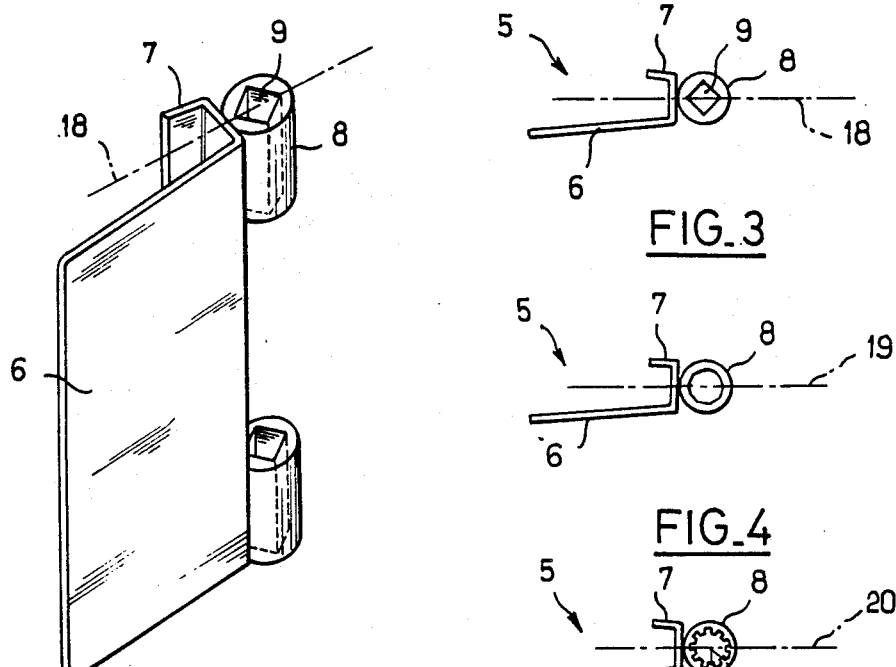
FIG_2
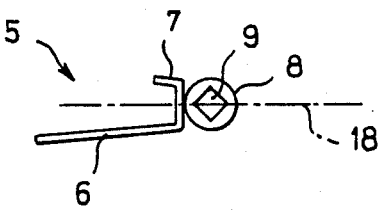
FIG_3
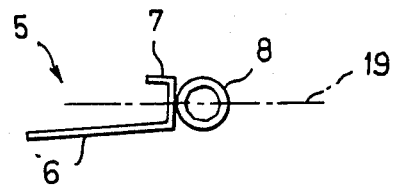
FIG_4
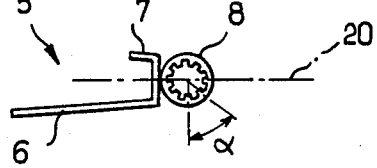
FIG_5

STERNAL RETRACTOR

BACKGROUND OF THE INVENTION

The invention relates to a sternal retractor, intended more particularly for operations on the mammary arteries.

For surgical operations on the heart and the lungs, sternal retractors have been used for a very long time which are introduced between the two parts of the sternum after having cut it. The sides are then gradually separated by moving apart the two arms of the retractor by means of a rack. The valves mounted on the arms of such retractors fit over the sternum and the beginning of the ribs, the separation taking place in the plane of the rack parallel to the body of the patient in a latero-lateral way. Such retractors are perfectly suitable for operations on the heart and the aorta as well as on the lungs and neighboring regions.

However, following new medico-surgical treatments, operations are more and more often carried out on the mammary arteries particularly for coronary bridges. Now, these are situated on the internal face and on each side of the sternum and are therefore inaccessible when conventional retractors are used and it is difficult and dangerous to operate on said vessels.

So attempts have been made to perfect a sternal retractor adapted for this type of operation and it has been discovered that it is possible to separate the parts of the sternum not parallel to the body of the patient but by raising one with respect to the other anteo-posteriori, by using a sternal retractor of the invention. Retractors generally may also be called spreaders.

SUMMARY OF THE INVENTION

Such a sternal retractor includes on one of the arms a removable bearing valve whose axis is in a plane forming an angle of 30° to 60° with a plane of the rack and, on the other arm, two removable blades in the form of closed claws, mounted loosely on a round rod.

So as to be able to operate successively on both mammary arteries, if required, the retractor is reversible and, for that, the oblique blade has a U shape of which the leg intended to bear on the internal face of the sternum is shorter than the leg bearing on the external face and is fitted onto a shaft at the end of the corresponding arm by means of fittings pierced with a hole oriented obliquely with respect to the legs of the blade. Two claws of the other arm are mounted on a fitting pierced with a round hole and fitted onto a round rod forming the arm carried by the slider of the rack.

In a particular case, the axis of the bearing blade is in a plane forming the angle of 45° with the plane of the rack and, in this case, the shaft ending the arm of the rack is a square shaft and the hole in the fittings is a square hole one of whose diagonals passes through the axis of the bearing blade.

In order to obtain angles of 30° to 60°, which are required for adapting to different morphologies, shafts may be used with the corners cut off at the end of the arm carrying the bearing retractor element and polygonal holes of the same type provided in the fittings, or if a more accurate adjustment of the angle between the retractor element and the rack is desired, a grooved support shaft may be used with a hole grooved correspondingly so as to allow the angle to be modified by a smaller or greater value depending on the pitch of the grooving. Other configurations allowing adjustment of the angle to be obtained while maintaining the characteristics of reversibility of the apparatus may of course be considered and form part of the field of the invention.

To facilitate reversal of the handle of the rack, this latter is extended by a toothless section.

BRIEF DESCRIPTION OF THE DRAWINGS

Other features and advantages of the invention will be clear from reading the detailed description of the invention, with reference to the accompanying drawings in which:

FIG. 1 is a perspective view of the sternal retractor of the invention,

FIG. 2 is a perspective view of a bearing blade of the invention,

FIG. 3 is a top view of the blade of FIG. 2, and

FIGS. 4 and 5 are views similar to FIG. 3 showing other hole configurations.

DESCRIPTION OF THE PREFERRED EMBODIMENT

FIG. 1 shows the sternal retractor 1 of the invention mounted for operating on the left mammary artery, which operation is the most current. However, as already mentioned, the retractor is reversible and allows operation on the right mammary artery. The following description is made first of all by considering the retractor mounted for an operation on the left mammary artery and then reversal of the retractor will be described for operating on the right mammary artery.

The sternal retractor of FIG. 1 is moreover designed for the case where it is simply desired to obtain an angle of 45° between the planes of the retractor element and the rack. Other possibilities will be described hereafter with reference to FIGS. 4 and 5.

The sternal retractor 1 is formed of a toothed rack 2 having at its left hand end (in FIG. 1) an arm 3 extended by a shaft 4 of square section. The rack and the arm are advantageously made as a single piece, contrary to what happens in conventional retractors. In fact, the resistance exerted by the body of the patient is much higher when retraction takes place in the plane of the body of the patient and when one side is raised with respect to the other. The forces which are exerted on a conventional retractor lead to manufacturing the rack and the arm in two parts, the arm further forming a heel beyond the rack. In the retractor of the invention, such a heel does not exist which results in slightly reducing the dimensions of the part of the retractor in contact with the body of the patient and so in limiting the risks of damaging organs. The cross section of arm 3 can have any form and will generally be rectangular like that of the bar forming the rack. Shaft 4 is carried by arm 3 so that two of the faces of the square are parallel to the plane of the rack. On this shaft 4 is fitted a bearing blade 5 in the form of a slightly open U with two unequal legs 6 and 7. For this, the flat part of the bearing blade has at both ends a fitting 8, preferably cylindrical, pierced with a square hole 9 disposed so that the axis 18 of the blade passes through the diagonal of the square hole. Consequently, when the blade is fitted on shaft 4, the legs of the U are in planes forming an angle of 45° with the plane of the rack. The blade 5 is fitted on shaft 4 so that the longest leg 6 of the U is above the sternum, the short leg 7 coming into position there below with the advantage that it does not come into contact with the underlying organs.

The slider 10 of the rack is formed in a conventional way by a stirrup 11 having, at its lower part, two rollers driven by the handle 12, these rollers not being visible in the drawings (a gear wheel is not used for it raises cleaning problems). This part of the slider does not form part of the invention, and will not be described in greater detail. On the other hand, the right hand arm and the blades which it supports form part of the invention. Arm 13 is formed by a cylindrical rod mounted on the stirrup of slider 10. Two blades 14 and 15 are mounted loosely on arm 13. These two blades are in the form of claws so that they do not slip on the tissues which they hold apart, but closed so as not to injure them. These claws are mounted on rods of different legs for the two retractor elements 14 and 15, ending in a cylindrical fitting 16 pierced with a bore, also cylindrical, whose diameter is very slightly greater than that of arm 13 so as to be able to slide freely thereon; the upper end of arm 13 includes a stud 17 and the bore of fittings 16 has a groove of a depth corresponding to the height of the stud. Thus, the fittings can be fitted onto arm 13 by positioning the groove opposite the stud, but preventing untimely sliding of the blades from the arm during use of the retractor. The blade 14 with the longest rod is placed above the blade 15 of the shortest rod so as to accommodate the curvature of the sternum. The blades 14 and 15 are mounted so that the concave part of the claws is directed towards arm 13.

The retractor is used as follows: once the sternum has been cut, the surgeon places the bearing blade 5 on the right hand part (in the case of FIG. 1) of the sternum and places the blades 14 and 15 on the left hand part, while adjusting the relative position in height on the rod, the two arms 3 and 13 being of course in a closed up position. When the surgeon then actuates the handle of the rack so as to move arm 13 away, the long leg 6 of the blade 5 bears on the sternum and since it is in a plane at 45° with respect to the plane of the rack, blades 14 and 15 move the other half of the sternum away while raising it. The left mammary artery is then very readily accessible and the surgeon may operate without difficulty.

If it is necessary to operate on the right mammary artery, after bringing arms 3 and 13 together, the surgeon removes the retractor and reverses its direction of use so that the rack remains at the lower level of the approach path. For this, he disengages the slider carrying arm 13, removes blades 14 and 15 and fits them on again in the other direction, removes the bearing blade and repositions it in the other direction after turning it through 180°, turns over the retractor so that arm 13 is at the right and engages the slider on the rack so that the handle is on the outside. With conventional retractors, which do not have to be reversed, the slider is fitted on the rack in a sterile chamber before the surgical operation, by an operator who has all the time necessary for correctly positioning the slider with respect to the teeth of the rack. On the other hand, during an operation the surgeon has little time for carrying out this delicate task whose difficulty is increased by the relatively large weight of arm 13 which may cause the slider to tilt downwards when attempting to fit it on the first tooth of the rack. To facilitate this task, the toothed rack 2 of the retractor of the invention is extended by a toothless section 17, of a length corresponding substantially to that of the slider, which allows this latter to be fitted sufficiently for it to be stabilized on the rack; positioning of the handle of the slider then takes place automatically with respect to the teeth of the rack.

FIGS. 4 and 5 shows two other possibilities of the configurations of the hole formed in the fittings mounting the blade 5 in FIG. 4, this hole has 12 equal faces allowing the angle to be adjusted by steps of 15°, thus readily providing values of 30, 45 and 60° for the angle between the axis 19 of the bearing element 5 and the plane of the rack, this axis 19 passing through two opposite apices of the 12 sided hole pierced in the fittings of the element. In the case of FIG. 5, the hole is a groove hole whose axis 20 passes through two opposite groove apices and which is fitted on a shaft 3 having complementary grooves. Thus the angle between the retractor element and the rack may be varied by increments, by modifying it each time by a value corresponding to the angle $\alpha$ between two grooves, this angle being very often smaller than that shown in FIG. 5 which is relatively large for the sake of clarity of the Figure.

Of course, shaft 3 ending arm 4 is oriented appropriately with respect to axes 19 and 20 so that there always exists an angle between the plane of the shaft of the blade and the plane of the rack.

The sternal retractor such as described above is made, like conventional retractors, from stainless steel treated so as to have the required mechanical strength.

What is claimed is:

1. A sternal retractor comprising an elongated toothed rack having a longitudinal axis and two arms supporting blades, wherein one arm of said arms has a polygonal perimeter, and said retractor further comprises a mounting means for carrying a removable bearing blade on said one arm, said removable blade comprising two legs and a connecting piece between said legs, said mounting means including a portion having a polygonal shape which corresponds to the polygonal shape of said one arm perimeter for co-operating with such one arm perimeter to mount said bearing blade on said one arm, said mounting means portion polygonal shape including a plurality of apices, and being oriented to have a pair of said apices located along an operating axis which extends perpendicular to said connecting piece and which is located in the middle part of said connecting piece, said mounting means and said one arm being oriented with respect to said rack so that said operating axis forms an angle of 30° to 60° with the longitudinal centerline said rack, whereby the sternum is retracted in an antero-posterior way, and the other arm is a round rod carrying two removable blades in the form of closed claws, said blades being loosely fitted on said round rod whereby they may take any angular orientation with respect to the bearing blade and be located at any desirable position along the length of the rod, the arms and the blades being so designed that the sternal retractor is fully reversible.

2. A sternal retractor as claimed in claim 1, wherein said bearing blade is in the form of a slightly open U with two legs of unequal length.

3. A sternal retractor as claimed in claim 1, wherein said one arm ends in a shaft whose cross section is polygonal and the bearing blade includes mounting fittings pierced with a hole of the same configuration as the cross section of the operating shaft and oriented so that the axis of the bearing blade passes through two opposite apices of the polygon.

4. A sternal retractor as claimed in claim 1, wherein said one arm ends in a shaft whose cross section is grooved and the bearing blade includes mounting fittings pierced with a hole of the same configuration as the cross section of the shaft and oriented so that the operating axis of the bearing blade passes through two opposite apices of the grooving.

5. A sternal retractor as claimed in claim 3, wherein said one arm ends in a shaft of square section and the bearing blade includes two mounting fittings pierced with a square hole disposed so that the operating axis of the bearing blade passes through a diagonal of the square hole, the angle obtained being thus of 45°.

6. A sternal retractor as claimed in claim 1, wherein the blades in the form of closed claws are mounted on rods of different lengths ending in fittings pierced with a bore.

7. A sternal retractor as claimed in claim 6, wherein said bore of the fittings for the claw shaped blades further includes a groove and the arm on which these blades are mounted includes a stud at its upper end.

8. A sternal retractor as claimed in claim 7, wherein the toothed rack is extended by a toothless section.

9. A sternal retractor comprising a toothed rack having two arms supporting blades, wherein one of said arms carries a removable bearing blade in the form of a slightly open U with two legs of unequal length and a connecting piece comprising a planar face between said legs and said bearing blade having an operating axis in a plane perpendicular to the middle part of said planar face, said one arm ending in a shaft of square section, said bearing blade including two mounting fittings each pierced with a square hole and disposed on the shaft so that the operating axis of said bearing blade passes through a diagonal of the square hole, and the other arm is a round rod comprising a stud at its upper end and carrying blades in the form of closed claws mounted on rods of different lengths ending in fittings pierced with a bore, said bore including a groove cooperating with said stud, and said toothed rack is extended by a toothless section.

10. A sternal rectractor comprising a toothed rack having two arms supporting blades, wherein one of said arms carries a removable bearing blade in the form of a slightly open U with two legs of unequal length and a connecting piece comprising a planar face between said legs and said bearing blade having an operating axis in a plane perpendicular to the middle part of said planar face, said one arm ending in a shaft of grooved section, said bearing blade including two mounting fittings each pierced with a grooved hole and disposed on the shaft so that the operating axis of said bearing blade passes through two opposite apices of said hole, and the other arm is a round rod comprising a stud at its upper end and carrying blades in the form of closed claws mounted on rods of different lengths ending in fittings pierced with a bore, said bore including a groove cooperating with said stud, and said toothed rack is extended by a toothless section.

* * * * *